US008026095B2

(12) United States Patent
Krieg

(10) Patent No.: US 8,026,095 B2
(45) Date of Patent: Sep. 27, 2011

(54) BIOLOGICAL PRODUCTION OF ETHANOL FROM WASTE GASES

(76) Inventor: Ingo Krieg, Jacksonville, FL (US)

(*) Notice: Subject to any disclaimer, the term of this patent is extended or adjusted under 35 U.S.C. 154(b) by 1098 days.

(21) Appl. No.: 11/809,640

(22) Filed: Jun. 2, 2007

(65) Prior Publication Data

US 2008/0299650 A1    Dec. 4, 2008

(51) Int. Cl.
*C12M 1/04* (2006.01)
(52) U.S. Cl. ............... 435/298.1; 435/300.1; 435/161; 435/266
(58) Field of Classification Search ........... 435/292.1, 435/293.1, 294.1, 300.1, 298.1, 161, 266; 47/1.4
See application file for complete search history.

(56) References Cited

U.S. PATENT DOCUMENTS

| | | | | |
|---|---|---|---|---|
| 2,732,663 A * | 1/1956 | Dewey | ............................ | 47/1.4 |
| 2,854,792 A * | 10/1958 | Juda | ........................ | 435/257.3 |
| 6,136,577 A | 10/2000 | Gaddy | | |
| 2003/0211585 A1 | 11/2003 | Gaddy et al. | | |
| 2005/0260553 A1* | 11/2005 | Berzin | ............................ | 435/3 |

* cited by examiner

*Primary Examiner* — William H Beisner
(74) *Attorney, Agent, or Firm* — Arthur Yeager P.A.

(57) ABSTRACT

Apparatus for biological production of ethanol from waste gases includes a bioreactor including a plurality of tunnels each having inlet and outlet passageways, a gasifier reactor generates a continuous supply of syngas from waste gases into the upper portion of each tunnel. A mixing device provides a continuous supply of fermentation microbes in a liquid directed by pumps and spray misters into the tunnel. Pumps direct the liquid vertically for conversion of the syngas into ethanol.

18 Claims, 8 Drawing Sheets

BIOLOGICAL PRODUCTION OF ETHANOL FROM WASTE GASES

CROSS-REFERENCE TO RELATED APPLICATION

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of the Invention

This present invention is directed towards improving a process utilizing a continuous gaseous waste stream (syngas) through a tunnel fermentation system or tunnel bioreactor under anaerobic conditions.

2. Relevant Art

Previous methods and art of waste gas fermentation involved tanks or tower structures containing the fermentation medium such as a Continuously Stirred Reactor (CSTR) and Immobilized Cell Reactor (ICR). Most demonstrated tanks in the art are of the Continuously Stirred Reactor (CSTR) type and keep the incoming syngas in solution longer to prevent large bubble formation because syngas would co-mingle to a larger a larger bubble as it ascended to the surface without agitation. Previous art needed to have the syngas pressurized to 3 atmospheres (42 lbs) for it to be pumped against the force of 20-30 feet of water solution. Once the syngas has surfaced there is no longer any contact with the ethanol producing microbes and the exposed syngas must be separated for its unused components or combusted to make electricity. The present invention allows for the syngas, primarily composed of $CO$, $CO_2$ and $H_2$, to slowly meander at very low pressures (less than 5 lbs psi) through a tunnel.

Contact with the anaerobic bacterium *Clostridium Ijungdahlii* or mixture of microbes with the meandering syngas must be accomplished by pumping the microbial aqueous medium and allowing contact above the aqueous medium surface level.

Previous methods in the art of ethanol production from carbon black waste gas have all been in a continuous stirred bioreactor.

Carbon black waste gases are produced as the result of partial oxidation of hydrocarbons with insufficient air to form amorphous carbon, with about 1.2 pounds of carbon monoxide produced per pound of elemental carbon. These waste gases form a serious atmospheric contamination problem but also represent a valuable chemical feedstock resource not presently being recovered.

Previous methods in the art have included carbon black waste gas containing about 14% $CO$, 17% $H_2$, 4% $CO_2$ and its major component $N_2$ and is agitated by compressed air into a continuous stirred tank reactor and maintained at 37 degrees C., and contains *Clostridium Ijungdahlii* isolate ER12 ATCC deposit 55380. The gas retention time is maintained at 0.52 min. The aqueous liquid medium containing water, base salts, B-vitamins, a nitrogen source and a sulfide source is fed into the reactor at a liquid dilution rate (defined as the ratio of the liquid flow rate to reactor volume) of $1.05\ hr^{-1}$. The agitation rate of this reactor is 322 rpm, the temperature is 37 degrees C. and the operating pH is 5.03. Under these conditions, the conversion of $CO$ was 83% and the conversion of $H_2$ was 54%.

Optimal gas retention times in (CSTR) models using agitation were in the range of three minutes and 1000 rpm on the bench scale model. The gas recovery varies with its uptake by the bacteria, which was in turn a function of the cell density. See U.S. Patent Application, J. L. Gaddy, Pub. No. US 2003/0211585 A1, Nov. 13, 2003.

There remains a need in the art of fermentation of industrial gaseous substrates also known as syngas for an improved handling system to allow optimal exposure of syngas for the production of ethanol.

BRIEF SUMMARY OF THE INVENTION

In one aspect of the present invention there is provided apparatus for biological production of ethanol from waste gases comprising a bioreactor including at least one tunnel having upper and lower portions and including a plurality of inlet passageways and a plurality of outlet passageways, a gasifier reactor for generating syngas from waste gases and providing a continuous supply of syngas into the upper portion of the at least one tunnel through one inlet passageway, a mixing device for supplying fermentation microbes in a liquid into the lower portion of the at least one tunnel through another passageway, and pumping means for directing the liquid vertically into the upper portion into the syngas for providing for contact between the microbes and the syngas for conversion of the syngas into ethanol. Further included is at least one spray mister located in the upper portion receiving the liquid through another inlet passageway for providing contact between the microbes and the syngas for conversion of the syngas into ethanol. The pumping means includes at least one propeller pump located in the liquid in the lower portion. The at least one tunnel includes a plurality of walls for defining a U-shaped interior space to increase the length of time the microbes and the syngas are in contact. Alternately, the at least one tunnel includes a plurality of walls for defining a double S-curve interior space to increase contact between the microbes and the syngas. The liquid includes a species of microbes being *Clostridium Ijungdahlii* isolate ER12 ATCC deposit 55380. The liquid includes nutrients for the microbes and the continuous supply of the gasifier reactor provides the syngas including $CO$, $CO_2$ and $H_2$. The inlet and outlet passageways are located to provide for substantially horizontal flow of the syngas and the liquid to increase the length of time the syngas and the microbes are in contact for increasing the conversion efficiency of the syngas into ethanol.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Introduction

Figure 1:
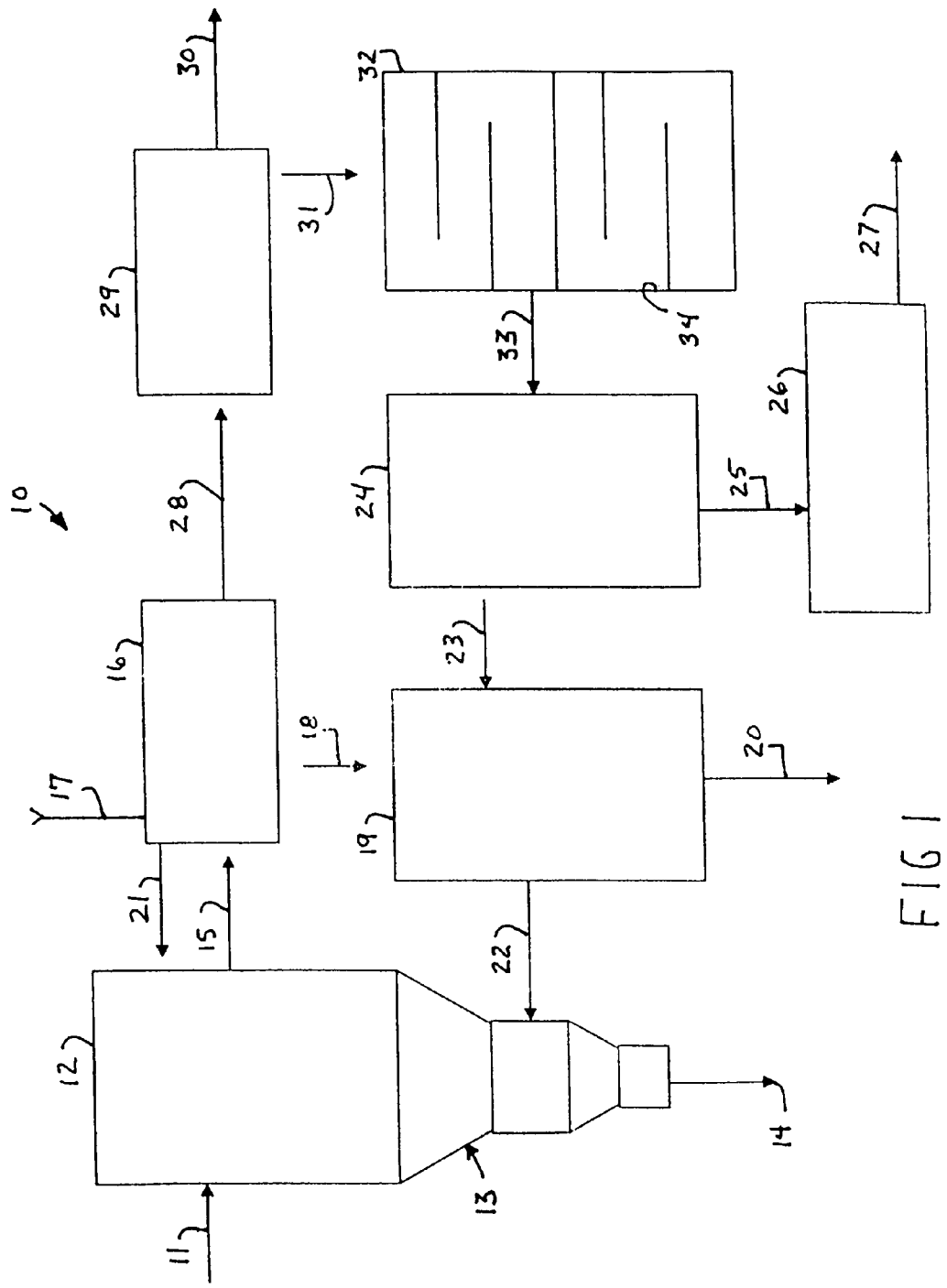
FIG. 1 is a simplified block diagram of synthetic gas (syngas) flow in accord with the present invention.

The term "syngas" as used herein means carbon monoxide and hydrogen mixed with other elements or compounds, including carbon dioxide, nitrogen and methane, in a gaseous state and which are typically released or exhausted to the atmosphere either directly or through standard combustion. This exhaust syngas is normally released via smokestack temperatures and pressures into the atmosphere. Prior art has improved the exhaust by using vertical fermentation tanks and shown syngas to be processed there-in into products that include, but are not limited to acetic, prop ionic, and butyric acids; methanol, ethanol, propane, and n-butane; plus salts. The process of the present invention includes a tunnel fermentation system using a spray mist system. It is important for the microbe laden water to come in contact with the carbon monoxide and hydrogen molecules floating in the large volume of air emissions coming from the reactor. An air tunnel is suitable for converting these atmospheric pollutants into useful products and allows for larger quantities of syngas and longer period of time for the fermentation process to take place.

The spray mist contains anaerobic bacteria that are known to convert carbon monoxide and water or hydrogen and carbon dioxide into alcohols and acids and acid salts. This list of known bacteria includes *Acetobacteruimkivui, A. woodii, Clostridium aceticum, Butyribacteriummethylotrophicum, C. acetobutylicum, C. formaoaceticum, C. kluyveri, C. thermoaceticum, C. thermocellum, C. thermohydrosulfuricum, C. thermoscchaolyticum, Eubacterium limosum, C. Ijungdahlii* PETC and *Peptostreptococcus productus*. Anaerobic bacteria known to produce hydrogen from carbon monoxide and water include *Rhodospirillum rubrum* and *Rhodopseudomonas gelatinosa*. All the aforementioned may be selected as microbes of this invention.

In addition to these listed bacteria, two strains of additional clostridia which produce acetic acid or ethanol from CO and $H_2O$ or $H_2$ and $CO_2$ have been isolated. One is a *Clostridium Ijungdahlii* ER12 rod-shaped, gram positive, non-thermophilic anaerobe which operates at a low pH and gives superior acetic acid yields. Increased exposure or hang time for the given bacteria greatly enhances the recovery of the product.

*C. Ijungdahlii* ER12 carries out a vigorous acetogenic fermentation of glucose. It also infrequently forms spores and carries out a primarily acetogenic fermentation of hexose or $H_2:CO_2$. It is motile with peritrichous flagellation. This new strain of *C. Ijungdahlii*, referred to as ER12, was isolated from a natural water source and was deposited on Dec. 8, 1992, with the American Type Culture Collection (ATCC), Rockville, Md., accession no. 55380.

In the process of the present invention, "mixed strains" of the bacteria enumerated hereinabove may be utilized in the spray. By mixed strains, it is meant a mixed culture of two or more anaerobic bacteria. This mixed strain, when utilized in the spray process described herein, produces organic acids, salts, alcohols, hydrogen, SCP, etc.

New strains of anaerobic bacteria have been isolated which enable the syngas conversion with high efficiency. Modifications to the fermentation conditions can result in the production of ethanol instead of acetic acid in some strains. Depending on the specific microorganism(s) utilized, variables which must be considered in forming products from waste gases include nutrient constituents and concentrations, pressure, temperature, gas flow rate, medium flow rate, medium pH, inoculum level, maximum product concentrations to avoid inhibition.

A hollow fiber membrane cell recycle unit is used to maintain a cell concentration of 10.5 g/L inside the reactor. Water (medium) from extraction is sent back to the fermentation tunnel as recycle.

With reference now to the drawings, a block diagram of the syngas flow in the tunnel fermentation system (TFS) in accord with the present invention is shown at numeral 10 in FIG. 1. The first step in the conversion process is the formation of superheated syngas 15 by way of introducing carbon-based input material 11 into a gasifier reactor 12 continuously heated to 800°-1110° C. via heating apparatus 13. Slag 14 is removed through the bottom of reactor 12 and includes toxins trapped therein.

The superheated syngas 15 exits reactor 12 at approximately 850° C. and enters heat exchanger 16. Fresh water 17 is turned into steam 18 which is directed to steam generator 19 which in turn is used in electric power generator 20 by conventional means as understood in the art. In addition, fresh, preheated air 21 is sent to heat exchanger 16 to provide air at approximately 500° C. into reactor 12 to introduce needed oxygen therein. Spent steam 22 is sent to reactor 12 for thermal hydrolysis of $H_2O$. Moisture is necessary for the additional hydrogen and oxygen for chemical structuring in the reactor 12.

The second major step in the present method includes cooling the superheated syngas 15 via heat exchanger 16. The cooled syngas 28 is then directed to scrubber 29 to remove various undesirable byproducts 30, principally chlorines and sulfurs. Cleaned syngas 31 is then provided to a tunnel bioreactor 32. The cooled syngas 31 is between 37°-39° C., which temperature is necessary for the microbes 34 in bioreactor 32.

The conversion of syngas 31 in bioreactor 32 creates a syngas substrate 33 that will have about 50% of the original volume as much of input 31 has been converted to ethanol in output gas 33. The remaining substrate gas 33 including unused CO and $H_2$ is combusted in steam boiler 24 which provides steam 23 to generator 19. Catalytic converter 26 removes $NO_x$ compounds from boiler output gas 25 and provides cleaner output gas 27.

Figure 2:
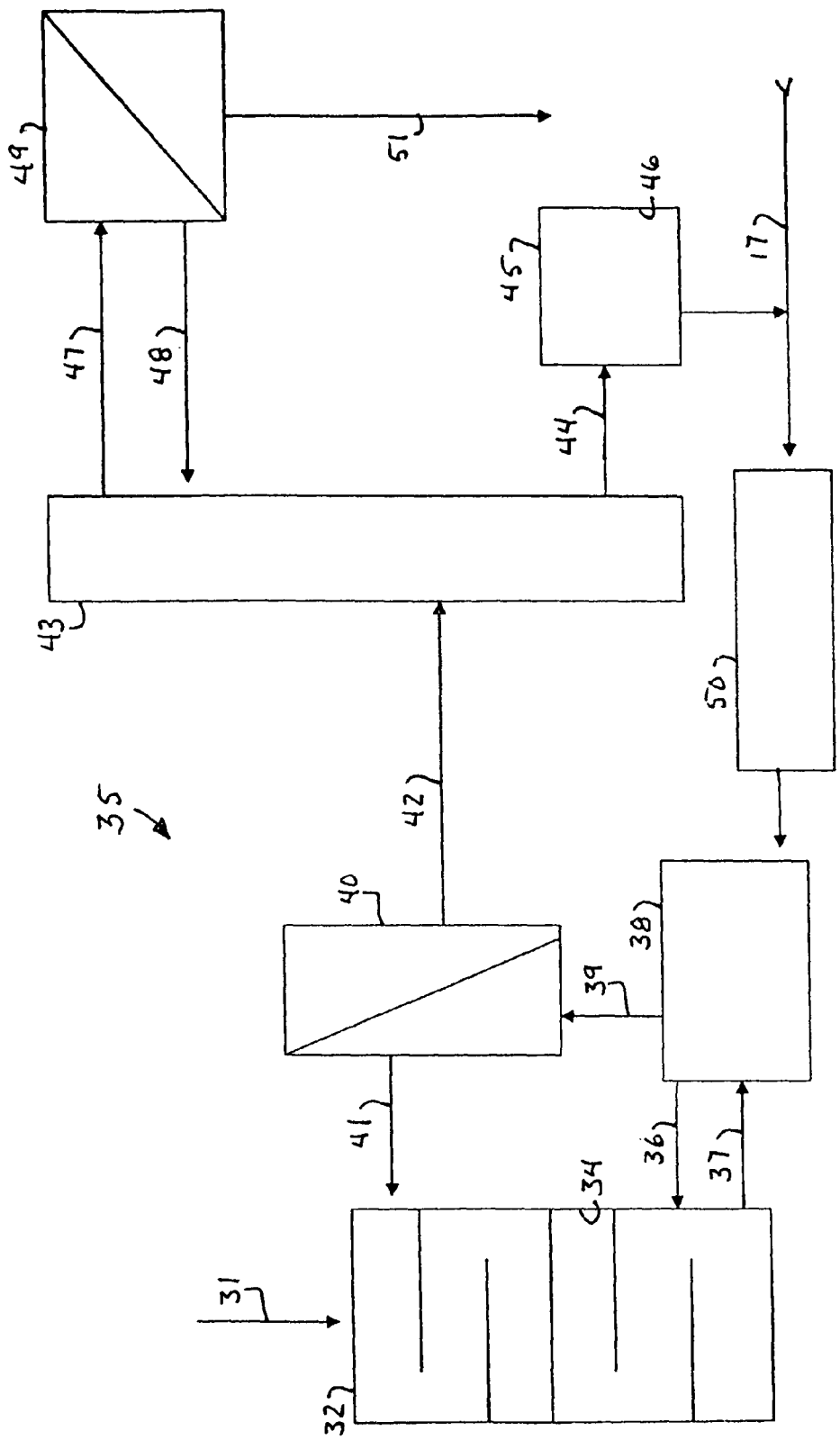
FIG. 2 is a simplified block diagram of the ethanol liquid medium flow in accord with the present invention.

With reference now to FIG. 2, the ethanol liquid medium flow is shown at numeral 35. Tunnel bioreactor 32, including microbes 34 therein, receives clean syngas 31 from scrubber 29 (FIG. 1). The first step in the fermentation-to-distribution process includes the creation of the nutrient mix input 37 which is derived from nutrient pre-mixer 45 combining nutrient premix 46 with distillation and fresh water 44, 17. Input 37 is sent to heat exchanger 50 and to pumping station 38.

The nutrient media will vary based upon the type of anaerobe 34 chosen and the desired end product. The pre-mix nutrients 37 are constantly fed into tunnel bioreactor 32. The culture resides in bioreactor 32. The chosen microbes 34 live dispersed throughout the liquid and spray mixing stages as will be discussed hereinbelow.

The syngas 31, rich in CO and $H_2$, is continually introduced into tunnel bioreactor 32. In the present invention the syngas 31 is retained in the bioreactor for a longer period of time than prior art vertical bioreactors that use compressed air and high agitation to reduce bubbling. The generally horizontal and substantially enclosed tunnel bioreactors 32 in accord with the various embodiments maximize efficiency of the conversion process by allowing for an exposure or "hang time" of 5-10 minutes for available CO and $H_2$ compared to less than a half minute for vertical bioreactors.

The nutrient mix input 37 is pumped via station 38 into spray misters 67 (FIGS. 7 an 8) located strategically inside the tunnel bioreactor to allow maximum uptake of airborne nutrients. A portion 39 of the output from station 38 is diverted to filtration device 40, in the form of a centrifuge, for example, or other apparatus to recover microorganisms.

To maintain a high cell concentration, syngas-ingesting microbes 41 from device 40 are returned to tunnel bioreactor 32 allowing for a faster reaction rate and cell life cycle. Tunnel effluent 36 is also directed to device 40 to control microbe concentration levels as desired.

Once the microbes 41 are controlled at the desired level, the remaining liquid 42 from device 40 is sent to distillation processor 43 which produces 95% ethanol 47 that is further processed into anhydrous ethanol 51 via molecular screen 49. Further distillation of screened effluent 48 allows the water form distillation 44 to be replenished in mixer 45 and sent back to the bioreactor via station 38.

Figure 3:
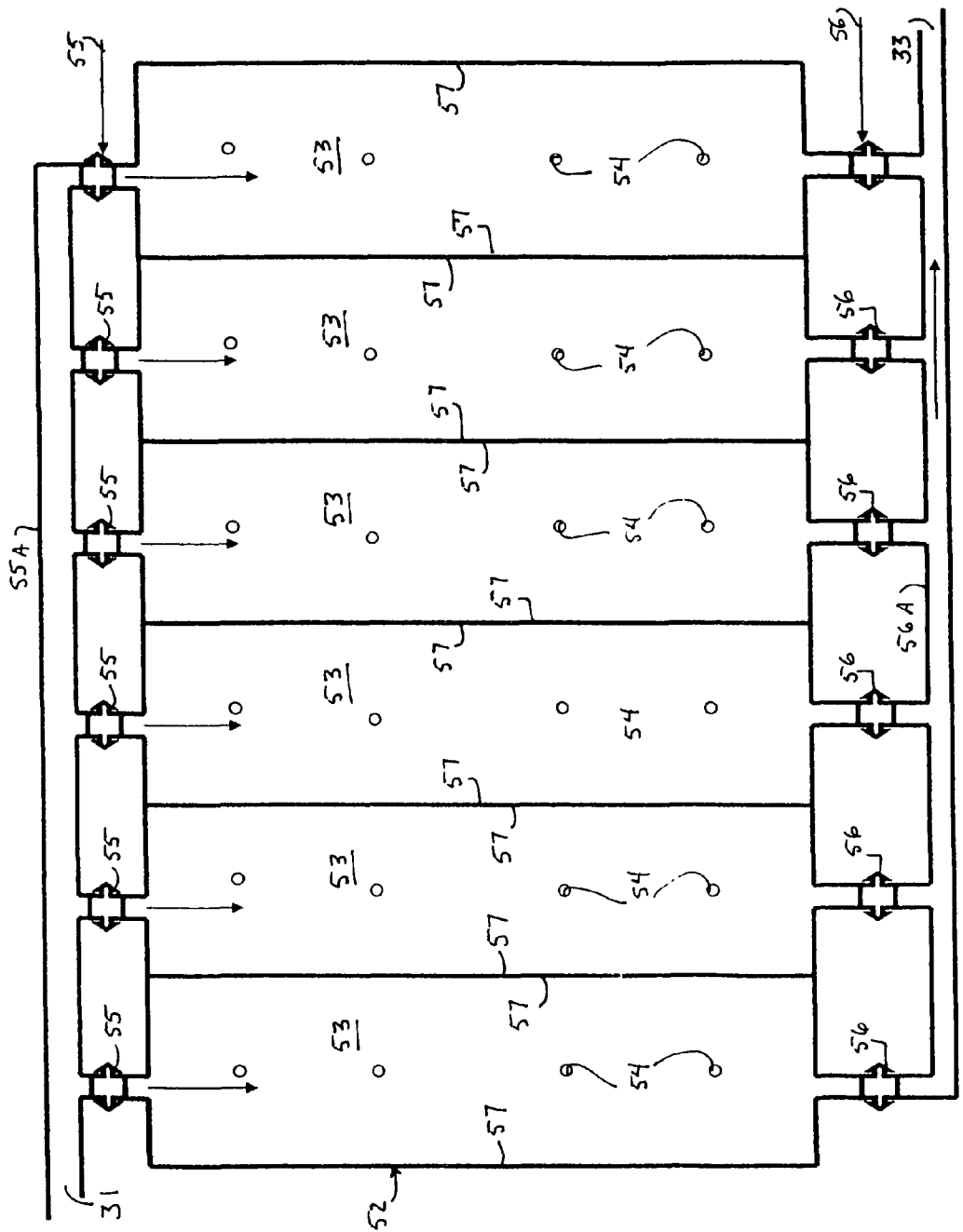
FIG. 3 is a top view of the tunnel bioreactor in accord with the present invention showing multi-row tunnels.

One embodiment of tunnel bioreactor 52 is shown in FIG. 3. A series of tunnels 53 receive syngas 31 which travels horizontally via a plurality of entry valves 55. Unused syngas substrate gas 33 exits a respective tunnel 53, defined by enclosed walls 57 via exit valves 56 and goes to steam boiler 24 (FIG. 1). Drains 54 provide effluent 36 to pumping station 38 for filtration at device 40.

Figure 4:
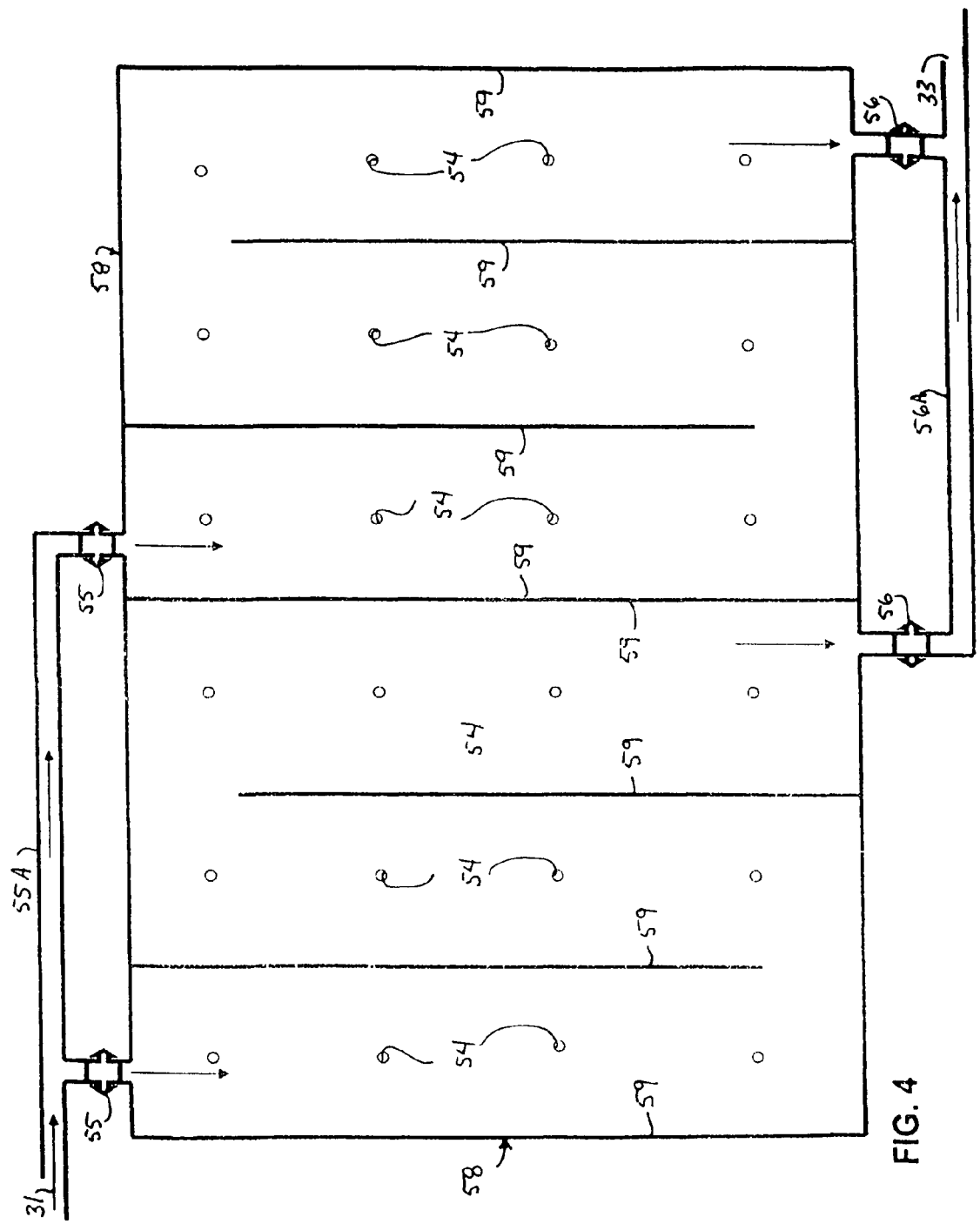
FIG. 4 is a top view of a double S-curve tunnel in accord with the present invention.

FIG. 4 illustrates two "double-curve" tunnels 58 as another embodiment of bioreactor 32. Syngas is directed via walls 59 into double-S interior spaces in a substantially horizontal direction to increase conversion efficiency. This embodiment reduces the number of valves 55, 56 needed. Drains 54 are as before as is unused gas 33.

Figure 5:
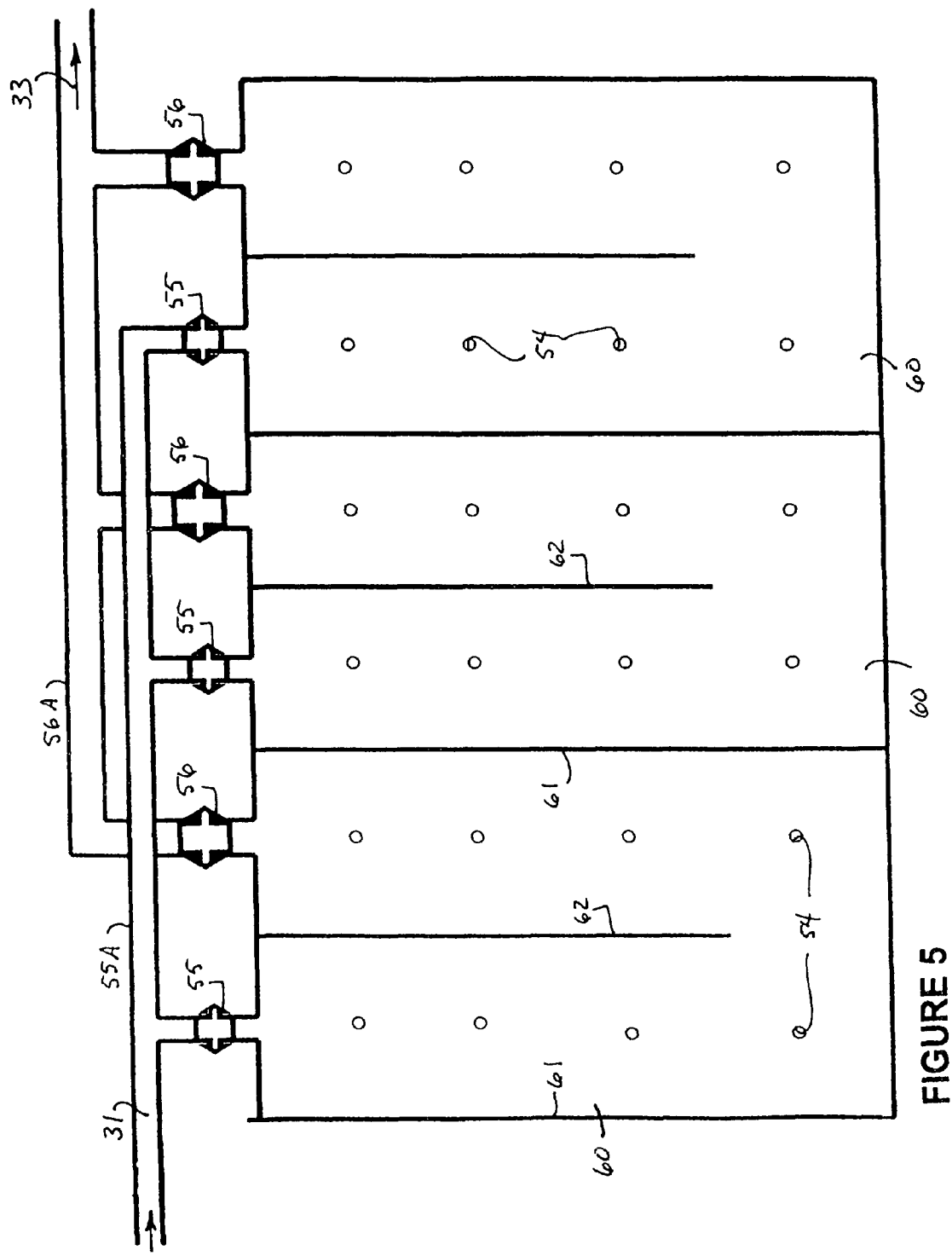
FIG. 5 is a top view of consecutive U-shaped tunnels in accord with the present invention.

FIG. 5 illustrates three "U-shaped" tunnels 60 as part of another embodiment of bioreactor 32 formed by walls 61 and 62 into U-shaped interior spaces. Walls 62 force syngas flow substantially horizontally through the distance of the tunnels 60 for maximum exposure time to microbes 44 in spray mist. Outlet pipes 56 are larger than entry 55 to reduce head pressure.

Figure 6:
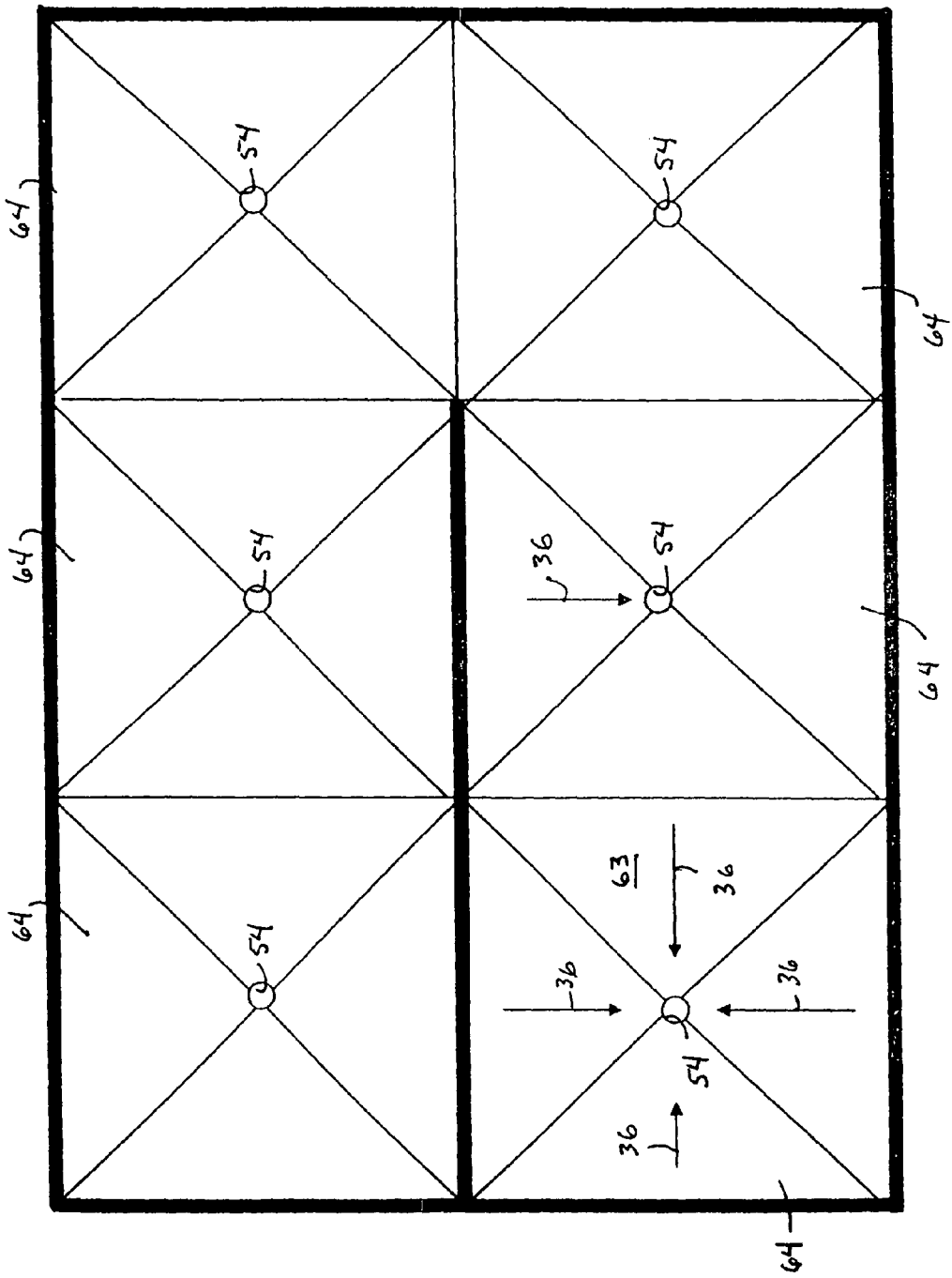
FIG. 6 is a top view of the tunnel floor drain pods in accord with the present.

FIG. 6 illustrates a top view of the sloping floors 63 used with each sector 64 of a tunnel bioreactor 32. Each drain 54 is at the center of a square sector or pod 64.

Figure 7:
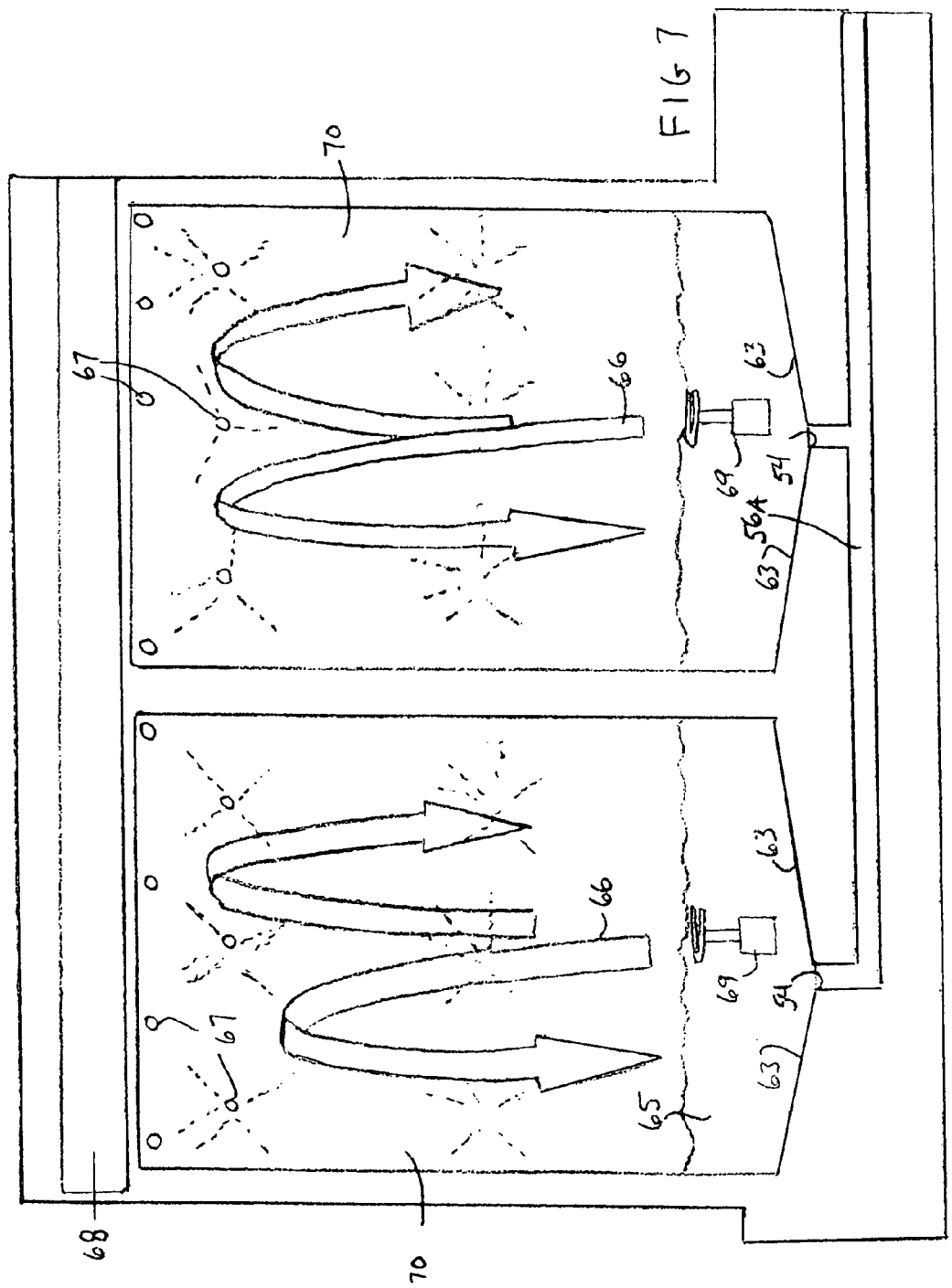
FIG. 7 is an end-sectional view of a U-shaped tunnel in accord with the present invention.

FIG. 7 illustrates an end sectional view of a U-shaped tunnel (FIG. 5). Liquid 65 is between a minimum of two feet in depth and a maximum of four to five feet. Totally submerged prop/motors 69 provide a vertical splash spray 66 upwardly into the syngas 70 above to provide a saturated liquid/syngas mix. The area occupied by syngas 70 is from at least twenty feet high and extends upwardly to thirty to forty feet high to provide as much fall time as possible to capture the available CO and $H_2$ for the production of ethanol. Spray misters 67 feed liquid into syngas 70 which falls into liquid 65 and exits through drains 54. A roof ceiling chamber 68 has a pressure of 3-5 lbs of $N_2$ filtered from exit gas after final combustion.

Figure 8:
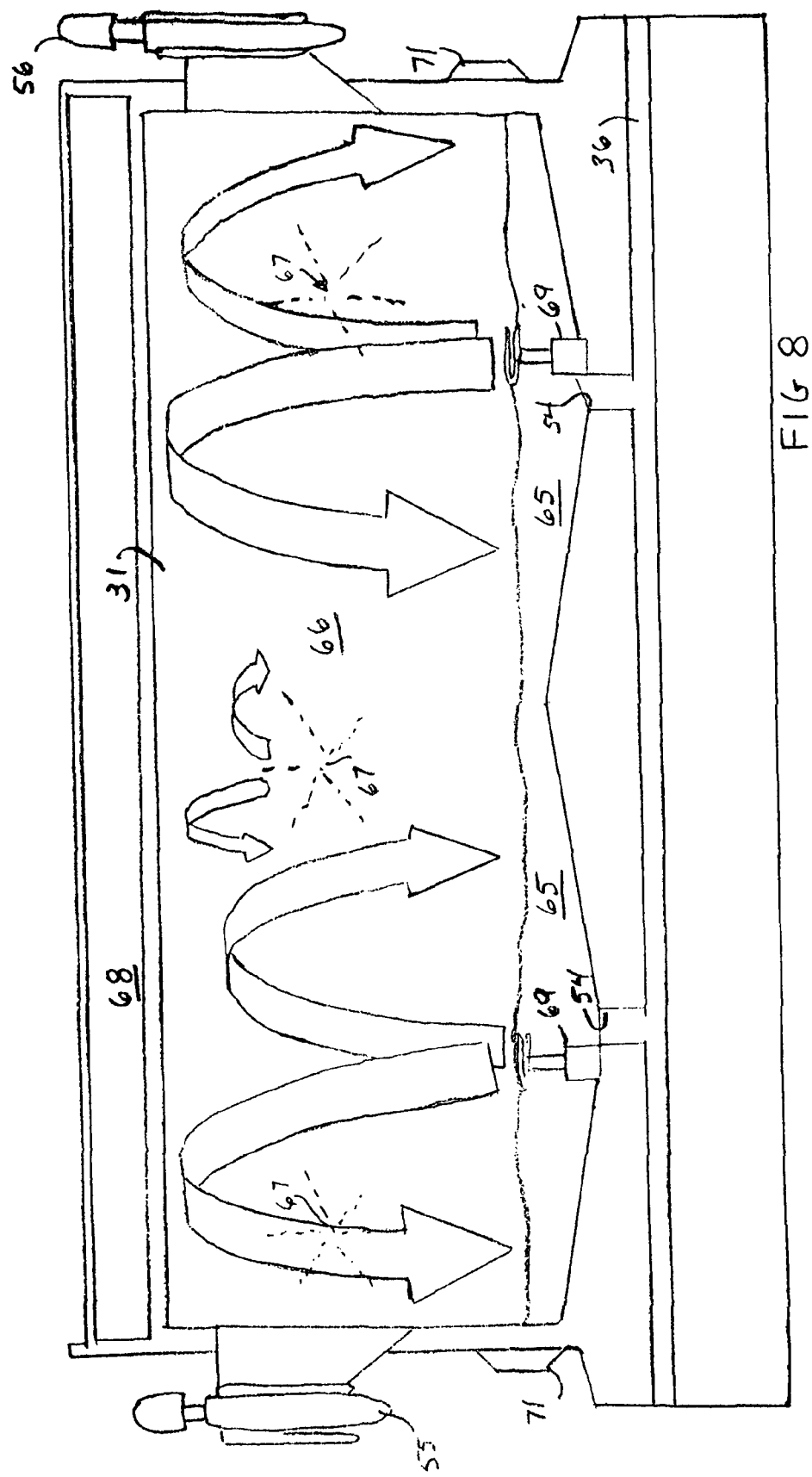
FIG. 8 is a side-sectional view of a single tunnel in accord with the present invention.

FIG. 8 illustrates a side-sectional view of a single tunnel which is substantially identical to the tunnel of FIG. 7. Manholes 71 provide for inspections as understood in the art.

The principal purpose of the syngas flow system as shown in FIG. 1 is the creation of clean, cooled syngas for supplying tunnel bioreactor 32 and the alternate tunnel constructions as illustrated. The specific construction shown provides the desired output in a manner that is clean and efficient.

The purpose of the medium flow shown in FIG. 2 is the continuous supply of anhydrous ethanol 51. Alternate constructions are possible as understood in the art.

Tunnel bioreactor 32 is believed to be unique in the art of syngas/ethanol conversion. Each tunnel is constructed to define an interior space, that, with the location of the inlet and outlet passageways, will provide a substantially horizontal flow that greatly increases the conversion efficiency of the process. The specific construction provides greatly increased time of contact between the microbes and the syngas to provide greater conversion than is possible with the systems known to the prior art.

The features of the present invention include:
1) The use of a Tunnel Fermentation System (TFS) provides an anaerobic condition for the production of alcohols, acids and salts from syngas derived from the pyrolysis of organic compounds.
2) A spray and mist system inside the TFS allows maximum exposure and increased time to enhance microbial production of end products.
3) The TFS can be U-shaped, circular or straight line, whichever configuration best suits the design engineering of the facility. U-shape is the preference.
4) The U-shaped design has a center wall completely dividing airflow going and returning to the plant, with the U turn diameter being equal to the width from outside to the center wall on the straight stretch.
5) Length of the TFS is flexible for maximum uptake of syngas components and may vary between facilities despite the plants having the same syngas capacity.
6) The TFS consists of adjoining water-filled basins with the microbe-containing liquid mixture a minimum of two feet to a maximum of four to feet in depth.
7) A surrounding exterior waterproof retaining wall a minimum of six feet in height supports walls and ceiling that are totally sealed.
8) An exterior building structure conceals and protects the TFS.
9) Intake and exhaust of unused syngas are the only openings in the TFS.
10) The TFS is designed to have separate basins square in shape with a sloping bottom.
11) Water levels are a minimum of six inches above the peak of each basin slope.
12) The center of each square sloping basin will have a drain that feeds a recirculating pump for the spray mist system and product extraction.
13) Multiple basins can feed the same re-circulating pump and can be isolated for periodic inspection for microbial buildup and constriction of pipe flow levels.
14) Temperature of the TFS will be between 37-39° C. for maximum activity for ethanol production and reproduction of microbes.
15) Blowers prior to the TFS will provide a very gentle 2 to 10 mph airflow allowing ample time for spray misting and the conversion of syngas components into useful alcohols, acids and salts.
16) A portion of the circulating mixture from the basin pumps is processed continually thru a series of filters, membranes and distillation columns. This "milks" the microbes of ethanol and also extracts some of the dead and live microbes.

17) A portion of the extracted microbes are returned to the TFS with the remaining strained and distilled water to keep microbial levels at optimum levels.
18) The microbial population reproduces very quickly and any excess is recycled to the gasifier for additional syngas production.
19) Each circulating pump will pull from their section of the TFS but will spray mist in all basins to allow for uniform digestion of syngas from beginning basin to end basin of the TFS.
20) Addition of nutrients and pH control for maximum microbial health is done every ten minutes to minimize fluctuations of pH and food value.
21) The TFS uses recirculation and spray misting of the water mix for agitation.
22) The TFS has a double layer for wall and ceiling material to protect the life anaerobic activity.
23) The TFS oreo center in walls and ceiling is a positive pressure area using pure nitrogen derived from an oxygen/nitrogen producing unit on site.
24) State of the art nitrogen seeking scanners monitor all air exposed surface areas to prevent larger tears and holes that may threaten the anaerobic microbes with exposure to oxygen.
25) The cross members of the TFS are filled with thread like filaments that serve as impilla.
26) Spray misters are mounted in the ceiling and on cross members strategically.
27) Multi-row tunnels have a distinct advantage of adding and deleting chambers as needed and storing nutrient medium laden with microbes as tunnels are emptied for inspections and then refilled.
28) The Tunnel Fermentation System has an air to liquid ratio that is far greater than traditional Continuous Stirred Reactors (CSTR) or immobilized Cell Reactors (ICR).

The described embodiments are preferably built at a single site of the appropriate size and location. Accordingly, the gasifier reactor 12 is included at the site. It is to be understood that the present invention is directed towards the production of ethanol from waste gases which are used in the production of syngas. A continuous supply of syngas is provided to the system from any appropriate source. The use of gasifier reactor 12 as an integral part of the production process is preferred.

While the invention has been described with respect to certain specific embodiments, it will be appreciated that many modifications and changes may be made by those skilled in the art without departing from the spirit of the invention. It is intended therefore, by the appended claims to cover all such modifications and changes as fall within the true spirit and scope of the invention.

What is claimed as new and what it is desired to secure by Letters Patent of the United States is:

1. Apparatus for biological production of ethanol from syngas comprising a bioreactor including at least one sealed tunnel having a lower portion defining at least one liquid holding basin and an upper portion defining a syngas space wherein the tunnel includes at least one syngas inlet and at least one syngas outlet positioned so as to allow said syngas to travel horizontally along the length of said at least one tunnel, wherein said at least one tunnel includes at least one liquid inlet positioned so as to introduce a liquid including microbes and at least one liquid outlet positioned so as remove liquid including microbes and wherein the horizontal length of said at least one tunnel allows contact between said microbes and said syngas for conversion of said syngas into ethanol; and a pumping device located within said lower portion for directing said liquid vertically into said upper portion into said syngas for providing contact between said microbes and said syngas for conversion of said syngas into ethanol wherein the apparatus further includes a gasifier reactor connected to said at least one syngas inlet for generating a syngas including CO, $CO_2$ and $H_2$ from waste gases and providing a continuous supply of syngas into said upper portion of said at least one tunnel through said at least one syngas inlet.

2. The apparatus as defined in claim 1 further including at least one spray mister located in said upper portion receiving said liquid through said at least one liquid inlet for providing contact between said microbes and said syngas for conversion of said syngas into ethanol.

3. The apparatus as defined in claim 1 wherein said at least one tunnel includes a plurality of walls for defining a U-shaped interior space to increase the length of time said microbes and said syngas are in contact.

4. The apparatus as defined in claim 1 wherein said at least one tunnel includes a plurality of walls for defining a double S-curve interior space to increase contact between said microbes and said syngas.

5. The apparatus as defined in claim 1 wherein said at least one tunnel is dimensioned such that said lower portion can maintain said liquid at a depth from two to five feet and said upper portion provides a syngas space from at least twenty feet high to forty feet high.

6. The apparatus as defined in claim 1 wherein said at least one tunnel is defined by walls and a ceiling that include chambers or positive pressure areas for containing nitrogen gas.

7. The apparatus as defined in claim 1 wherein said pumping device is a propeller pump.

8. Apparatus for biological production of ethanol from syngas comprising a bioreactor including at least one sealed tunnel having a lower portion defining at least one liquid holding basin and an upper portion defining a syngas space wherein the tunnel includes at least one syngas inlet and at least one syngas outlet positioned so as to allow said syngas to travel horizontally along the length of said at least one tunnel, wherein said at least one tunnel includes at least one liquid inlet positioned so as to introduce a liquid including microbes and at least one liquid outlet positioned so as remove liquid including microbes and wherein the horizontal length of said at least one tunnel allows contact between said microbes and said syngas for conversion of said syngas into ethanol; and a pumping device located within said lower portion for directing said liquid vertically into said upper portion into said syngas for providing contact between said microbes and said syngas for conversion of said syngas into ethanol wherein said pumping device is a propeller pump.

9. The apparatus as defined in claim 8 further including at least one spray mister located in said upper portion receiving said liquid through said at least one liquid inlet for providing contact between said microbes and said syngas for conversion of said syngas into ethanol.

10. The apparatus as defined in claim 8 wherein said at least one tunnel includes a plurality of walls for defining a U-shaped interior space to increase the length of time said microbes and said syngas are in contact.

11. The apparatus as defined in claim 8 wherein said at least one tunnel includes a plurality of walls for defining a double S-curve interior space to increase contact between said microbes and said syngas.

12. The apparatus as defined in claim 8 wherein said at least one tunnel is dimensioned such that said lower portion can maintain said liquid at a depth from two to five feet and said upper portion provides a syngas space from at least twenty feet high to forty feet high.

13. The apparatus as defined in claim 8 wherein said at least one tunnel is defined by walls and a ceiling that include chambers or positive pressure areas for containing nitrogen gas.

14. Apparatus for biological production of ethanol from syngas comprising a bioreactor including at least one sealed tunnel having a lower portion defining at least one liquid holding basin and an upper portion defining a syngas space wherein the tunnel includes at least one syngas inlet and at least one syngas outlet positioned so as to allow said syngas to travel horizontally along the length of said at least one tunnel, wherein said at least one tunnel includes at least one liquid inlet positioned so as to introduce a liquid including microbes and at least one liquid outlet positioned so as remove liquid including microbes and wherein the horizontal length of said at least one tunnel allows contact between said microbes and said syngas for conversion of said syngas into ethanol; and a pumping device located within said lower portion for directing said liquid vertically into said upper portion into said syngas for providing contact between said microbes and said syngas for conversion of said syngas into ethanol wherein said at least one tunnel is defined by walls and a ceiling that include chambers or positive pressure areas for containing nitrogen gas.

15. The apparatus as defined in claim 14 further including at least one spray mister located in said upper portion receiving said liquid through said at least one liquid inlet for providing contact between said microbes and said syngas for conversion of said syngas into ethanol.

16. The apparatus as defined in claim 14 wherein said at least one tunnel includes a plurality of walls for defining a U-shaped interior space to increase the length of time said microbes and said syngas are in contact.

17. The apparatus as defined in claim 14 wherein said at least one tunnel includes a plurality of walls for defining a double S-curve interior space to increase contact between said microbes and said syngas.

18. The apparatus as defined in claim 14 wherein said at least one tunnel is dimensioned such that said lower portion can maintain said liquid at a depth from two to five feet and said upper portion provides a syngas space from at least twenty feet high to forty feet high.

* * * * *